United States Patent
Albiol Colomer et al.

(10) Patent No.: US 10,672,145 B2
(45) Date of Patent: Jun. 2, 2020

(54) DEVICE FOR EXTRACTING THREE-DIMENSIONAL INFORMATION FROM X-RAY IMAGES OF AN OBJECT, METHOD FOR CALIBRATING SAID DEVICE, AND METHOD FOR GENERATING SAID X-RAY IMAGES

(71) Applicants: Consejo Superior De Investigaciones Cientificas (CSIC), Madrid (ES); Universitat Politecnica de Valencia, Valencia (ES); Universitat de Valencia, Valencia (ES)

(72) Inventors: Francisco Javier Albiol Colomer, Valencia (ES); Alberto Corbi Bellot, Valencia (ES); Celso Bellot Romero, Madrid (ES); Alberto Albiol Colomer, Valencia (ES)

(73) Assignees: CONSEJO SUPERIOR DE INVESTIGACIONES CIENTIFICAS (CSIC), Valencia (ES); UNIVERSITAT DE VALENCIA, Valencia (ES)

( * ) Notice: Subject to any disclaimer, the term of this patent is extended or adjusted under 35 U.S.C. 154(b) by 263 days.

(21) Appl. No.: 15/563,312

(22) PCT Filed: Mar. 29, 2016

(86) PCT No.: PCT/ES2016/070216
§ 371 (c)(1),
(2) Date: Jan. 29, 2018

(87) PCT Pub. No.: WO2016/156646
PCT Pub. Date: Oct. 6, 2016

(65) Prior Publication Data
US 2018/0144501 A1 May 24, 2018

(30) Foreign Application Priority Data
Mar. 31, 2015 (ES) .................. 201530432

(51) Int. Cl.
*G06T 7/80* (2017.01)
*G06T 7/30* (2017.01)
(Continued)

(52) U.S. Cl.
CPC ................ *G06T 7/80* (2017.01); *A61B 6/585* (2013.01); *G06T 7/13* (2017.01); *G06T 7/30* (2017.01);
(Continued)

(58) Field of Classification Search
CPC .............. G06T 7/80; G06T 7/13; A61B 6/585
See application file for complete search history.

(56) References Cited

U.S. PATENT DOCUMENTS

2006/0262894 A1 11/2006 Bernhardt et al.
2009/0074136 A1 3/2009 Kamegawa
(Continued)

FOREIGN PATENT DOCUMENTS

JP 2011139761 A 7/2011
WO 2015011987 A1 1/2015

*Primary Examiner* — Hugh Maupin
(74) *Attorney, Agent, or Firm* — Hayes Soloway PC (57) ABSTRACT

Device for extracting three-dimensional information from radiographic images of an object; process for calibrating said device; and process for generating said radiographic images includes an X-ray emitter and an X-ray sensor. A contour sensor represents contour points of an object by means of the radiation emitted or reflected by the object. The device also has a calibration framework with X-ray markers, and contour markers. The processes are based on taking contour and X-ray images of the calibration framework, first without an object of study and subsequently with one, taking into account the information provided by the markers, and the fact that the contour sensor is placed in the same manner with respect to the X-ray emitter in all the images taken.

6 Claims, 5 Drawing Sheets

(51) Int. Cl.
*G06T 7/55* (2017.01)
*G06T 7/13* (2017.01)
*A61B 6/00* (2006.01)
*H04N 5/32* (2006.01)

(52) U.S. Cl.
CPC ............. *G06T 7/55* (2017.01); *H04N 5/32* (2013.01); *G06T 2207/10024* (2013.01); *G06T 2207/10116* (2013.01)

(56) References Cited

U.S. PATENT DOCUMENTS

| | | | |
|---|---|---|---|
| 2011/0054303 A1* | 3/2011 | Barrick | A61B 5/1077 600/424 |
| 2012/0294504 A1 | 11/2012 | Kyriakou | |
| 2015/0103969 A1 | 4/2015 | Flohr et al. | |
| 2016/0055639 A1 | 2/2016 | Hara et al. | |

* cited by examiner

DEVICE FOR EXTRACTING THREE-DIMENSIONAL INFORMATION FROM X-RAY IMAGES OF AN OBJECT, METHOD FOR CALIBRATING SAID DEVICE, AND METHOD FOR GENERATING SAID X-RAY IMAGES

OBJECT OF THE INVENTION

The present invention may be included within the technological field of medical application devices. More particularly, according to a first aspect of the invention, the object of the present invention relates to a device for extracting 3D information from radiographic images. According to a second aspect, the invention relates to a process for calibrating said device. According to a third object, the invention describes a process for generating said radiographic images.

BACKGROUND OF THE INVENTION

The taking of radiographic images of an object of study, whether a patient or an object, from different angles, positions and/or distances ("poses", a term that is widely used within this technological field), has acquired special relevance in fields such as medicine, surveillance and industrial production. In particular, it is very useful identifying, in a radiographic image, information corresponding to the location of points of interest which are present in other radiological image of the same object of study, which has been generated from a different location and/or orientation (pose).

This objective of obtaining several radiographic images of the object of study at different positions in order to obtain expanded information is typically performed using computed tomography (CT). However, in the case of industrial or medical applications, in which this technique is primarily used, such as for the preliminary analysis of the object of study, where efficient operation requires equipment that is modest and, at the same time, relatively fast, CT technology is particularly expensive and complex. Moreover, the use of CT instruments requires adopting a number of international principles related to safety and the ALARA radiological protection criteria.

There is an alternative, using only radiography systems, which has a lower cost and greater availability, but nonetheless is not exempt from the initial difficulty arising from the fact that the image produced is two-dimensional and, in order to perform a three-dimensional reconstruction, the relative locations of the source of X-rays with respect to the plate that acts as the X-ray sensor or the object of study are not known with sufficient precision. In other words, the pose of the system is not known. Moreover, it is complicated to obtain, from the record of several radiographic images, three-dimensional information about areas of interest that are simultaneously present in different shots from different distances and orientations. In particular, when the object of study is a patient, there are more strict requirements due to the underlying clinical interest.

SUMMARY OF THE INVENTION

The present invention provides a more affordable solution, in terms of cost and equipment availability, to the problem of extracting three-dimensional information from radiographic images, than the solutions offered in the current state of the art.

A first aspect of the invention describes a device for extracting three-dimensional information from radiographic images of an object. According to a second aspect of the invention, a process for calibrating the aforementioned device is described. According to a third aspect, the invention relates to a process for generating the aforementioned radiographic images.

The device comprises the following elements: an X-ray camera, a contour sensor, and a calibration framework, as explained below.

The X-ray camera is composed of an X-ray emitter and an X-ray receiver, with which radiographic images of an object of study are generated and taken, and, as explained below, under certain circumstances the radiographed object of study may be the calibration framework. Under other circumstances, the object of study may be another element that is to be subjected to examination. The object of study may also be a patient or an industrial product that is to be diagnosed and/or inspected.

The contour sensor is a device designed to obtain contour information about the scene and the objects, contributing to identify a plurality of contour points of the object of study and/or the calibration framework and/or the scene. This detection may be related to the capture of radiation that is directly present (and emitted) from the scene (including the object of study). The process for detecting the contour may also be based on the capture of radiation reflected by the object of study (and the scene, if applicable) having been previously irradiated from the contour sensor. This function may be performed by conventional cameras, depth cameras, or multi-spectral cameras.

The calibration framework is attached to the X-ray sensor. It comprises a plurality of markers, also called fiducial markers. On the one hand, the markers comprise X-ray markers, which are manually or computationally identifiable in radiographic images; and contour markers, also manually or computationally identifiable, against the radiation whereon the operation of the contour sensor is based.

The term "scene" represents the "set of spatial and temporal circumstances under which the acquisition of images" takes place. In the present document, it is translated as the relative joint arrangement of the X-ray emitter, the X-ray receiver, the contour sensor and the calibration framework. Likewise, the term "pose", which was previously identified, is understood to be the "posture or position adopted by a person that is to be photographed, sketched or painted by another". Within the context of the present document, it materialises in the relative position between two particular elements under consideration, such as, for example, the object of study with respect to the X-ray emitter, or the contour sensor with respect to the X-ray emitter.

In the prior art referred to in a previous section, there are limitations inherent to the information that may be obtained in an autonomous manner from the X-ray device. These limitations are related to the impossibility of obtaining contour information about the scene, such as the relative positions of the camera (X-ray emitter+X-ray receiver) in the coordinate system of the location of the device (generally the clinic), as well as the orientation of, or information about, the object of study. The present invention obtains said data, and integrates them in order to obtain three-dimensional information of a radiographic nature.

Moreover, the invention makes it possible for a professional, whether examining patients, or objects in industrial settings, to obtain scaling factors directly on radiographic images, which allows for a direct, reliable comparison of the dimensions that appear in said radiographic images, without the need to use external X-ray markers as a reference scale. Likewise, the need to define a specific calibration framework for each scene or pose, within the period of time when the device of the invention remains calibrated, is avoided.

On the other hand, according to a second aspect of the present invention, a process for calibrating the aforementioned device is presented. The calibration process comprises two steps.

In a first step of the calibration process, images, which are called first images, are taken of the calibration framework, preferably without the presence of the object of study. These first images comprise a first contour image, using the contour sensor, and a first X-ray image, using the X-ray camera. The position of the calibration framework with respect to the X-ray emitter and to the contour sensor is identical in the two first images. Likewise, the position of the contour sensor with respect to the X-ray emitter is also identical in both first images.

In a second step of the calibration process, starting from the first radiographic image and the X-ray markers, a matrix, called camera projection matrix ($P_x$), is determined which corresponds to a transformation that relates, with respect to the reference system attached to the X-ray sensor, the 2D coordinates of the points in the first radiographic image with the 3D coordinates of the points in space. From $P_x$, using well-known techniques, both the relative position between the contour sensor and the X-ray emitter, and the intrinsic parameters of the X-ray camera are determined, which are recorded in a matrix $K_x$. Similarly, from the first contour image, the relative position $D_x$ between the contour sensor and the X-ray sensor is determined, using the contour markers.

Finally, according to a third object of the present invention, a process for generating radiographic images that incorporate three-dimensional information is presented. In a first step of the process, images of the object of study jointly with the calibration framework are taken in at least two sessions, where each session comprises two second images: a second contour image, taken using the contour sensor, and a corresponding second radiographic image, taken using the X-ray emitter. In each of the sessions, the object of study has changed its position and/or orientation with respect to the contour sensor and/or the X-ray emitter and/or the X-ray sensor, although said position/orientation is the same for the two second images of the same session, for example, albeit not necessarily, by means of a simultaneous acquisition of both second images. Moreover, in all the sessions, the contour sensor remains stationary with respect to the X-ray emitter.

Therefore, the X-ray emitter may be oriented, in the different sessions, according to linear transformations $T_i$ composed of a rotation $R_i$ and a translation $t_i$ between the different sessions. In all the second images, the position of the contour sensor remains unchanged with respect to the X-ray emitter. In order to take the second images, only the contour markers are necessary.

In a second step of the process, the aforementioned corresponding rotations $R_i$ and translations $t_i$ are determined, using the contour markers in the second contour images and the second radiographic images, and taking into account that the contour sensor has moved jointly with respect to the X-ray emitter.

In a third step of the process, the affine transformation matrix for each of the sessions is determined from the recently calculated $K_x$ and the rotation $R_i$ and translation $t_i$. The information of matrix $P_i$ is subsequently used to determine the projection, in a second radiographic image i, of a point in another second radiographic image k.

BRIEF DESCRIPTION OF THE DRAWINGS

In order to supplement the description being made, and to contribute to a better understanding of the characteristics of the invention, according to a preferred embodiment thereof, a set of drawings is attached to said description as an integral part thereof, where the following is represented for illustrative, non-limiting purposes.

DETAILED DESCRIPTION OF THE INVENTION

With the aid of the aforementioned attached FIGS. 1-6, a detailed description of a preferred embodiment of the present invention is provided below.

According to a first aspect, the invention describes a device for extracting three-dimensional information from radiographic images of an object. According to a second aspect of the invention, a process for calibrating the aforementioned device is described. According to a third aspect, the invention relates to a process for generating the aforementioned radiographic images.

Figures 1, 2:
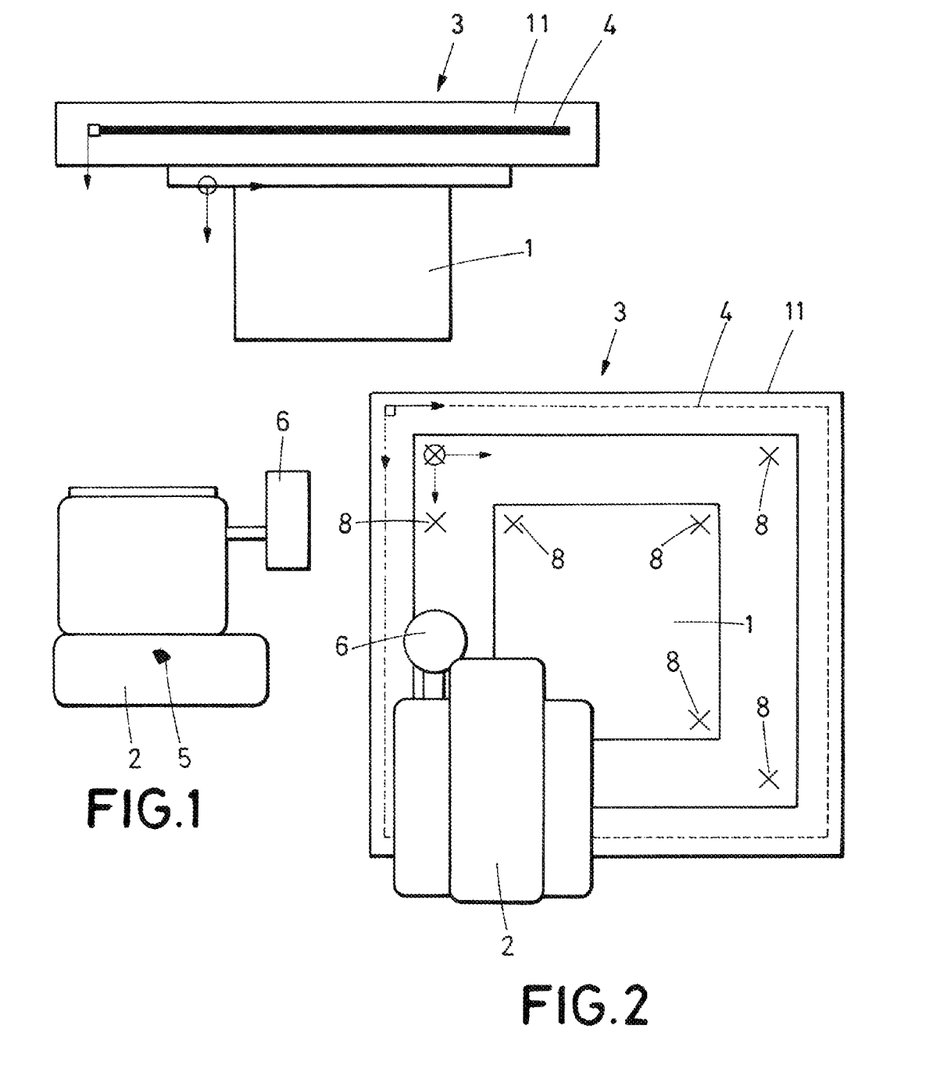
FIGS. 1 and 2.—Show corresponding schematic top (FIG. 1) and front (FIG. 2) views of the device of the invention.
Figure 3:
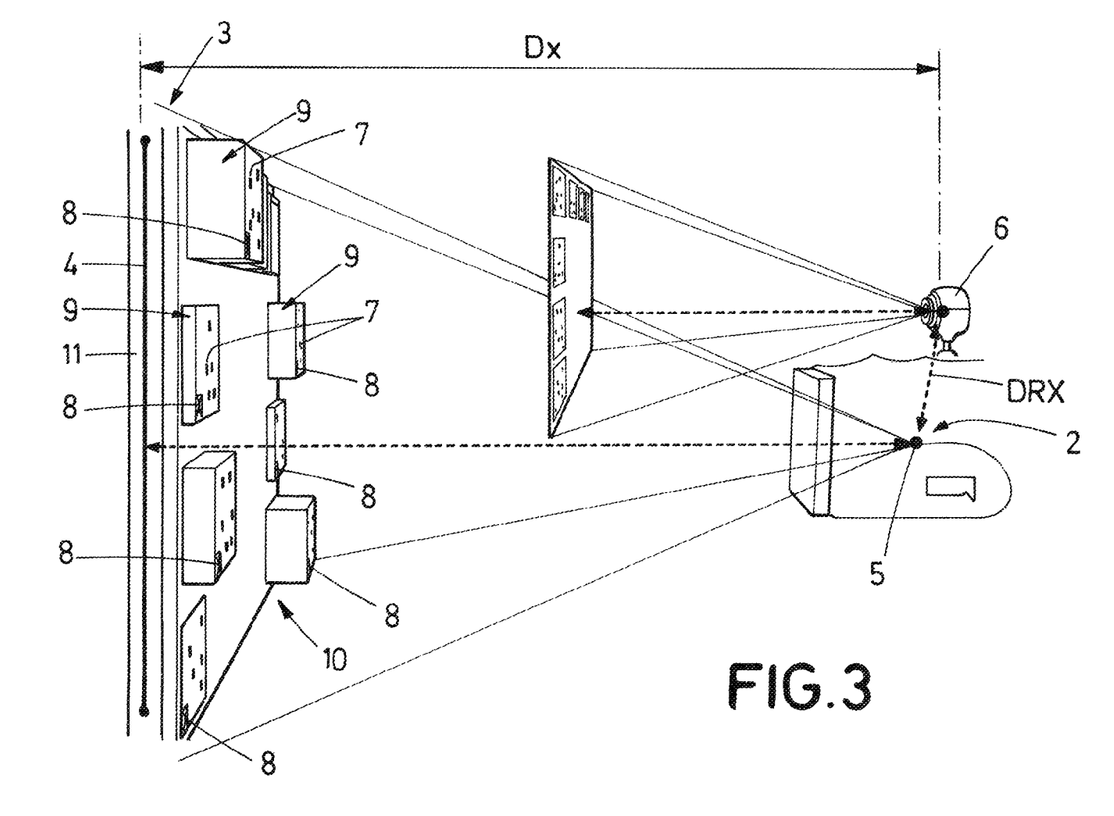
FIG. 3.—Shows a schematic image of the arrangement of the elements represented in FIG. 1, and the optical properties of the X-ray camera and the contour sensor.

As shown in FIGS. 1 to 3, the device of the invention comprises an X-ray camera (also called X-ray scanner) designed to take radiographic images of an object of study (1). The X-ray camera is composed of an X-ray emitter (2) and an X-ray sensor (3), also called plate, which defines an X-ray projection plane (4), for example a film, that may be subsequently subjected to some type of computerized processing, such as, for example: being digitalized, in the case of Computed Radiography (CR); or stored in the memory in situ, in the case of Direct Radiography (DR), or directly scanned from an imaging plate (IP). The optical characteristics of the X-ray camera are dependent upon the relative location (pose) between the X-ray emitter (2) and the X-ray sensor (3) in each radiographic image; for this reason, they are unknown in each case.

In the experiments performed, fixed 35×43-cm CR plates with a maximum resolution of 100 μm and FireCR™ plate readers were used. It has been verified that the successive arrangements and extractions of the plates do not affect the results obtained. In particular, it has been verified that the affine 2D-transformations between two X-rays taken from the same position and with the same plate mostly remain at a tolerance below 1 px and a 0.5% degree of tolerance. I.e. it may be assumed that, for all practical purposes, the plates and the plate-reading mechanisms behave as fixed radiological equipment. This verification was performed using the Insight Toolkit, from Kitware, between corresponding random pairs of radiographies.

The X-ray emitter (2) was modelled as a pinhole camera, wherein the diaphragm (5) of the X-ray emitter (2) simultaneously represents the anode and the optical centre. Since lenses are not involved, the effects associated with spherical aberrations, radial distortions and obliquity may be ignored, without a loss of generality.

The device further incorporates a contour sensor (6), which is understood to mean a device designed to identify a plurality of contour points of the object of study (1). The contour sensor (6) is preferably configured to capture radiation emitted and/or radiation reflected by the object of study (1). The contour sensor (6) may be, for example, a visible-light camera, an infrared camera, etc. More preferably, the radiation is visible radiation, such that the contour sensor (6) is preferably a visible-light camera, such as an RGB video camera, a depth camera, a combination of both, etc. In the example represented in the figures, the contour sensor (6) is an RGB video camera. The optical characteristics of the contour sensor (6) are considered to be known. A determination of said optical characteristics of the contour sensor (6) may be necessary, but said task is a well-known task within the technical field of the invention and is not considered to be an essential part of the invention.

The device of the invention further incorporates a plurality of markers (7, 8, 9), also called fiducial markers. The markers (7, 8, 9) are divided into contour markers (7), which offer contrast for the images generated by the contour sensor (6), and X-ray markers (8), which offer a contrast with the X-rays, as explained below.

The contour markers (7) present patterns of identifiable shapes by means of segmentation algorithms, and their dimensions and shapes are well-known. Preferably, the contour markers (7) present an essentially binary colour scheme. The configuration of the contour markers (7) and the position of one or several points of the contour markers (7), with respect to a first three-dimensional coordinate system attached to the X-ray sensor (3), are known. As explained below, the contour markers (7) make it possible to estimate the relative orientation and distance (pose) of the contour sensor (6) with respect to the first coordinate system attached to the X-ray sensor (3).

In turn, the X-ray markers (8) are manufactured with a material or materials that produce a contrast (generally due to differences in opacity) sufficient for X-rays, such as, for example, lead. The function of the X-ray markers (8) is to generate a legible, well-delimited symbol of the 2D projection represented in a radiographic negative, as explained further below in the description of the process of the invention. Moreover, the X-ray markers (8) present specific dimensions and a specific position with respect to a second coordinate system attached to the X-ray sensor (3). The first and the second coordinate system may be the same, but they may also be different, provided that the affine transformation between them is known. As explained below, the X-ray markers (8) make it possible to determine the relative position between the contour sensor (6) and the X-ray emitter (2) with respect to the second coordinate system.

Preferably, it is envisaged that some of the markers (7, 8) will be configured according to mixed markers (9), each of which incorporates a contour marker (7) and an X-ray marker (8) in a compact unit.

The set of markers (7, 8, 9), whether contour markers (7), X-ray markers (8) and/or, if applicable, mixed markers (9), is called calibration framework (10). According to a preferred embodiment, the calibration framework (10) is attached to the X-ray sensor (3) outside the area of interest of the X-ray sensor (3), i.e. in an area wherein the markers (7, 8, 9) affect the radiographic image as little as possible, for example in a structural component (11), such as a frame, of the X-ray sensor (3).

The calibration process of the second aspect of the invention comprises the following steps:

Firstly, the following are placed: the X-ray emitter (2) and the X-ray sensor (3), which make up the X-ray camera; the contour sensor (6); and the calibration framework (10), in an initial situation wherein both the X-ray emitter (2) and the contour sensor (6) are ready for operation and focus the X-ray sensor (3).

Subsequently, a calibration step is performed, which comprises two steps, described below.

Figure 4:
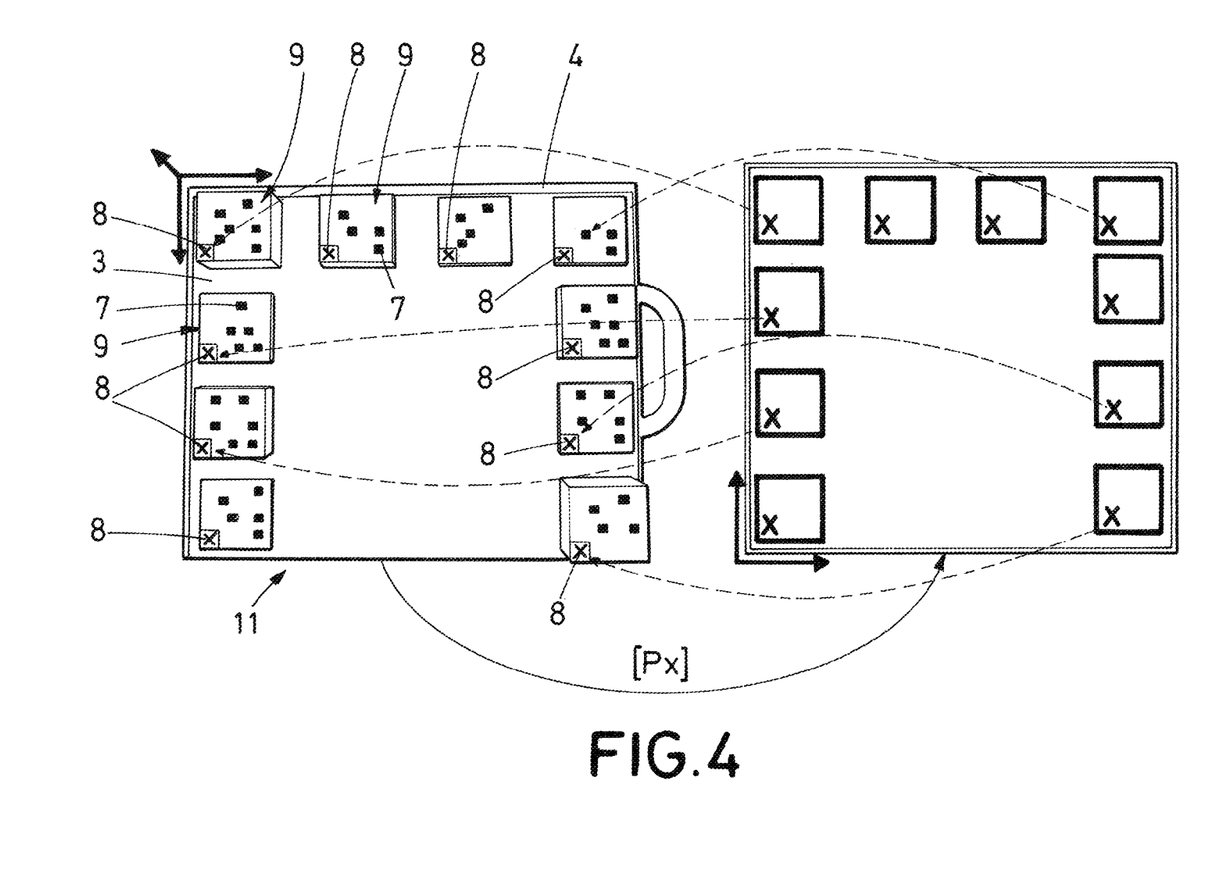
FIG. 4.—Shows a relationship between the calibration framework (left) and a first radiographic image (right) of said calibration framework, and represents the X-ray markers of the calibration framework in the first radiographic image.

According to a first step of the calibration process, which is illustrated in FIGS. 1, 2 and 4, two first images of the calibration framework (10) are taken; specifically: a first radiographic image, taken with the X-ray emitter (2), and represented on the right-hand side of FIG. 4; and a first contour image, taken with the contour sensor (6). The relative position between the X-ray sensor (3) and the X-ray emitter (2) must remain unchanged in the first contour image with respect to the first radiographic image. The same is applicable to the relative position between the X-ray emitter (2) and the contour sensor (6). It is not necessary to arrange the object of study (1) in order to take the first images, since this step is a prior step related to the determination of the relative locations, which involve the X-ray emitter (2), the X-ray sensor (3) and the contour sensor (6), and which, therefore, does not affect the object of study (1); for this reason, the object of study (1) is preferably not represented in the first images.

According to a second step of the calibration process, performed after the first step, from the first radiographic image, and using the X-ray markers (8), a matrix called camera projection matrix ($P_x$) is determined, which corresponds to an affine transformation that relates, with respect to the reference system attached to the X-ray sensor (3), the 2D coordinates of the points in the first radiographic image with the 3D coordinates of the points in space and, starting from $P_x$, using well-known techniques, both the relative position between the contour sensor (6) and the X-ray emitter (2), and the intrinsic parameters of the X-ray camera are determined, which are collected in a matrix $K_x$. Similarly, from the first contour image, the relative position $D_x$ between the contour sensor (6) and the X-ray sensor (3) is determined, using the contour markers (7).

With the previously described first and second steps of the calibration process, all the necessary data to characterize the behavior of the X-ray camera and the contour sensor (6) are obtained.

Once the calibration step has been performed, the device being described is ready to generate radiographic images wherefrom three-dimensional information may be extracted, as explained below.

In order to perform the aforementioned generation, we start from a device such as the one described above, which has been previously calibrated, or is at least calibrated, such that both $K_x$ and $D_x$ are known. According to a preferred embodiment, in order to obtain $K_x$ and $D_x$, the calibration method described above has been applied.

Figure 5:
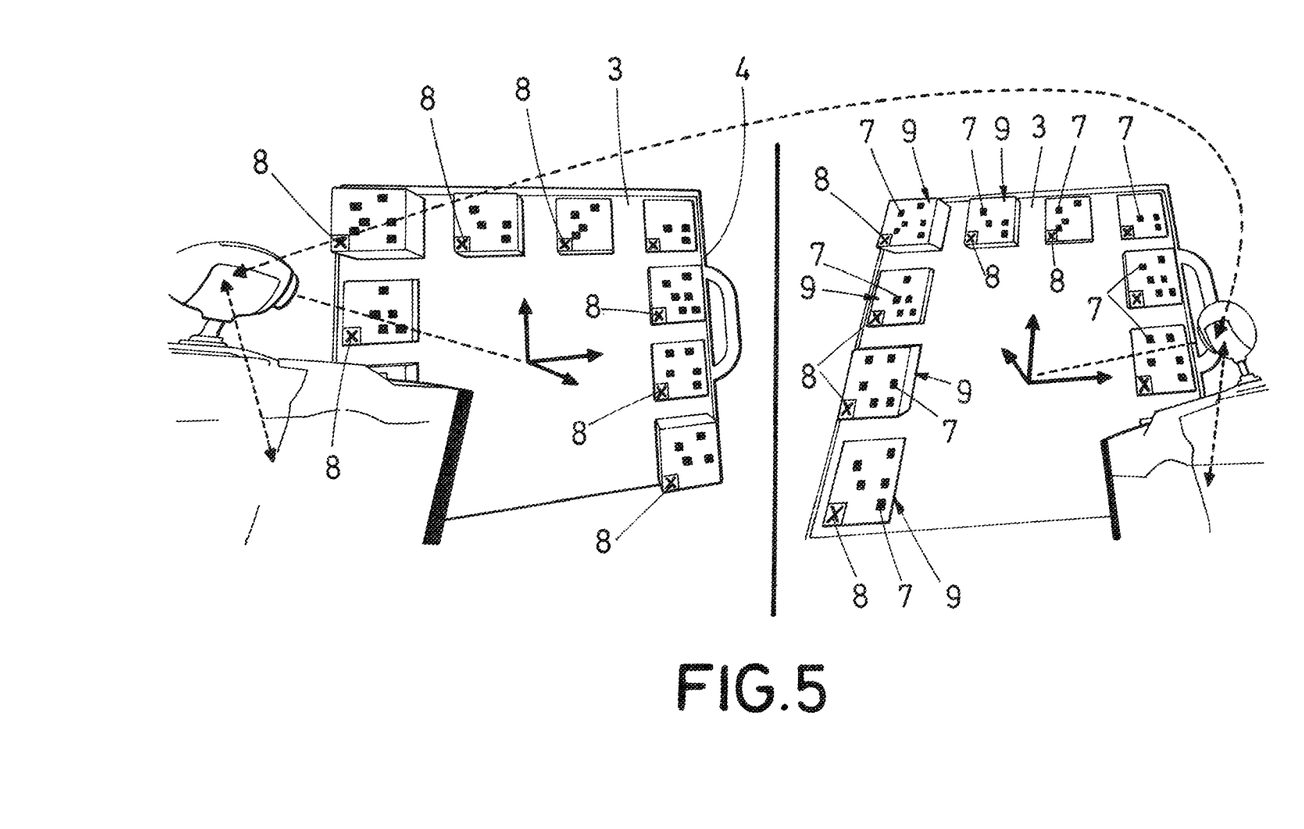
FIG. 5.—Shows two different poses of the X-ray emitter and the contour sensor with respect to the calibration framework, in order to take two sessions of second images, wherein the object of study is not represented.

Subsequently, images of the object of study (1) jointly with the calibration framework (10) are taken in at least two sessions, where each session comprises two second images: a second contour image, taken using the contour sensor (6), and a corresponding second radiographic image, taken using the X-ray emitter (2). In each of the sessions, the object of study (1) has changed its position and/or orientation with respect to the contour sensor (6) and/or the X-ray emitter (2) and/or the X-ray sensor (3), although said position/orientation remains the same for the two second images in the same session. Moreover, in all the sessions, the contour sensor (6) remains fixed with respect to the X-ray emitter (2), according to a relative position designated as DRX. FIG. 5 shows two positions, with respect to which the second images are taken.

The object of study (1) may move, whilst the X-ray emitter (2) and/or the X-ray sensor (3) and/or the contour sensor (6) remain static. Alternatively, the latter may move whilst leaving the object of study (1) static. It also possible that the object of study (1), the X-ray emitter (2) and the two sensors (3, 6) may all move. Any of the situations described is possible without a loss of generality, since the required computational complexity involved is within the reach of persons skilled in the art.

The above means that the X-ray emitter (2) may be oriented, with respect to itself, according to linear transformations $T_i$ composed of a rotation $R_i$ and a translation $t_i$ between the different sessions. In all the orientation images, the position of the contour sensor (6) remains unchanged with respect to the X-ray emitter (2).

In order to take the second images, only the contour markers (7) are necessary, so that, preferably, the X-ray markers (8), which, if applicable, are not a part of mixed markers (9), may be withdrawn, in order to prevent undesired effects, such as: excessive radiation dispersion; artifacts in the images; and, consequently, a more difficult reading of the images.

Since both for taking the first images and the second images, it is required that the contour sensor (6) and the X-ray emitter (2) have the same relative position and orientation, it is preferred that the contour sensor (6) and the X-ray emitter (2) be physically attached to one another.

Below the aforementioned corresponding rotations $R_i$ and translations $t_i$ are determined. To this end, first the two-dimensional coordinates of the visible light markers (7) in the second contour images are determined, and subsequently related to the three-dimensional coordinates for the visible light markers (7), which are known. From this, the rotations $R_i$ and translations $t_i$ related to the contour sensor (6) may be calculated. Since the contour sensor (6) has moved, in all the images, jointly with the X-ray emitter (2), said rotations $R_i$ and translations $t_i$ correspond to the previously defined rotations $R_i$ and translations $t_i$.

Subsequently, a corresponding associated projection matrix ($P_i$) is determined for each of the sessions, according to the following expression:

$$Pi = K_x * [R_i | t_i]$$

where $K_x$ is a matrix, previously defined in the calibration step, that incorporates the optical characteristics of the X-ray emitter (2).

Once the matrix $P_i$ corresponding to each second radiographic image i associated with each session has been determined, said matrices $P_i$ may be combined in order to add, to a given radiographic image i, information regarding a third dimension not represented in the radiographic image k. Below we explain an embodiment that illustrates a corresponding application of what has been explained above.

Figure 6:
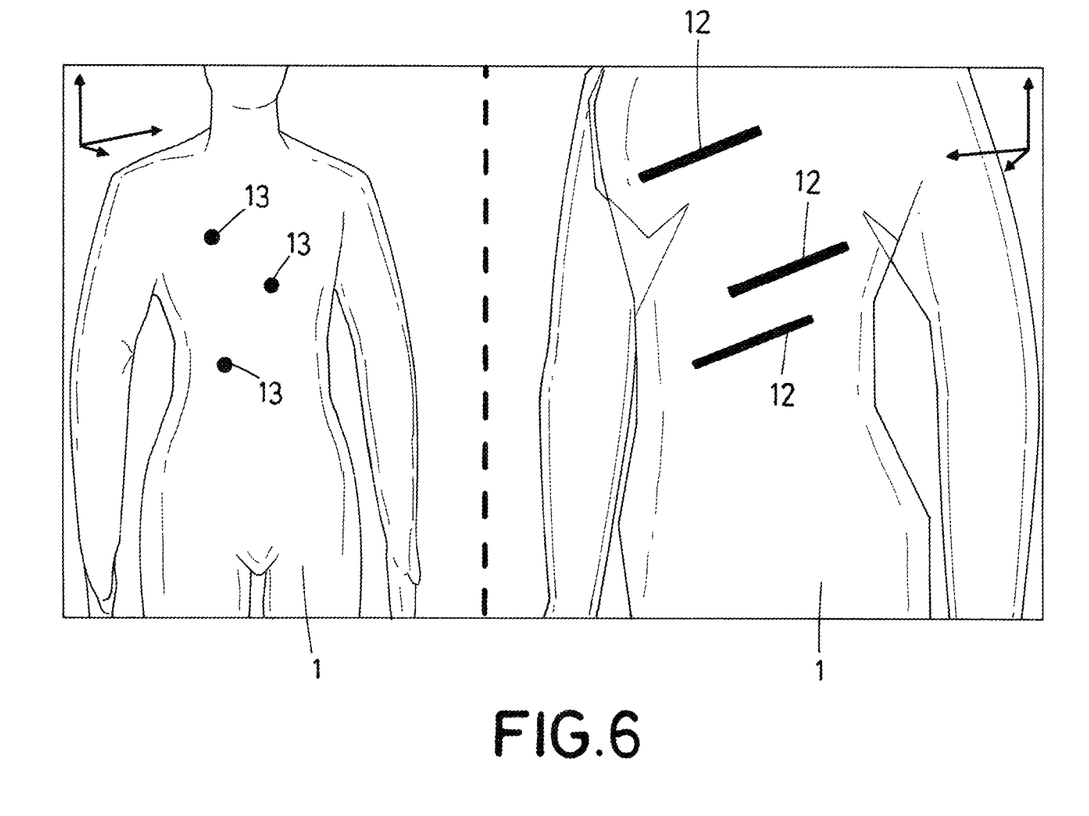
FIG. 6.—Shows two second radiographic images corresponding to different poses, where one of them (left) shows points of interest of the object of study, and the other (right) shows the epipolar lines corresponding to the points of interest.

According to a first example, the two-dimensional coordinates of a point of interest (13) in said radiographic image i are determined in a second radiographic image i. Subsequently, using computer processing, the following are determined: the beam defined by the point of interest in the image i, and the optical centre of the X-ray emitter (2), which, as mentioned above, coincides with the diaphragm (5), where the beam corresponds to an epipolar line (12) associated with the point of interest (13) in the second radiographic image i. Thereafter, using the aforementioned computer processing, and a matrix $P_k$, corresponding to a second radiographic image k taken with a different orientation, the second radiographic image k represents the epipolar line (12) corresponding to the point of interest (13) in the image i, where said representation may be computationally limited, if so desired, to the area with physical significance (that comprised within the object of study). In this way, it is possible to identify, in a second two-dimensional radiographic image k, the projection of the epipolar line (12) corresponding to the point of interest (13) in the second radiographic image i, which was not observed in said second radiographic image i.

The invention claimed is:

1. A process for calibrating a device for extracting three-dimensional information from radiographic images of an object, the device comprising:
    an X-ray camera, comprising an X-ray emitter and an X-ray sensor, for obtaining radiographic images of an object;
    an X-ray contour sensor, for capturing contour images that show contour points of the object, from radiation emitted or reflected by the object, on which radiation the contour sensor is based; and
    a calibration framework, attached to the X-ray contour sensor, comprising:
    a plurality of contour markers for providing a contrast against the radiation whereon the operation of the contour sensor is based; and
    a plurality of X-ray markers, for providing a contrast against X-rays,
wherein the object is selected from an object of study and the calibration framework; and wherein the calibration process comprises:
    taking a first contour image of the calibration framework, using the contour sensor and a first X-ray image, using the X-ray camera, where the position of the calibration framework with respect to the X-ray emitter and the contour sensor is identical in the two first images, and the position of the X-ray sensor with respect to the X-ray emitter is also identical in both first images;
    from the first radiographic image and the X-ray markers, determining a camera projection matrix ($P_x$), which corresponds to an affine transformation that relates, with respect to a reference system attached to the X-ray sensor, the 2D coordinates of the points in the first radiographic image with the 3D coordinates of the points in space;
    from the projection matrix $P_x$, determining both the relative position between the contour sensor and the X-ray emitter, and the intrinsic parameters of the X-ray camera, which get recorded in a matrix $K_x$; and from the first contour image, determining a vector $D_x$, which is representative of the relative position between the contour sensor and the X-ray sensor, using the contour markers.

2. The process of claim 1, wherein the object of study is not present when the first images are taken.

3. The process of claim 1, wherein at least one of the markers of the calibration device is a mixed marker that incorporates a contour marker and an X-ray marker in a compact unit.

4. The process of claim 1, wherein the calibration framework of the calibration device is attached to a structural component of the X-ray sensor, outside an area of interest of said X-ray sensor.

5. A process for generating radiographic images that contain three-dimensional information, the process comprising:
   a calibration process according to claim 1;
   and further comprising the following steps:
   taking images of the object of study jointly with the calibration framework in at least two sessions, where each session comprises two second images: a second contour image, taken using the contour sensor, and a corresponding second radiographic image, taken using the X-ray emitter, wherein, in each of the sessions, the object of study has changed its position and/or orientation with respect to the contour sensor and/or the X-ray emitter and/or the X-ray sensor, said position/orientation being the same for the two second images in the same session, and the relative position between the contour sensor and the X-ray emitter also being the same in all the second images, such that the X-ray emitter is oriented according to linear transformations $T_i$, composed of a rotation $R_i$, and a translation $t_i$ between the different sessions;
   determining the aforementioned corresponding rotations $R_i$ and translations $t_i$, using the contour markers in the second contour images and the second radiographic images, and taking into account that the contour sensor has moved jointly with respect to the X-ray emitter;
   determining an affine transformation matrix $P_i$, for each of the sessions, from $K_x$ and the corresponding previously calculated rotation $R_i$ and translation $t_i$;
   determining a corresponding projection, in a second radiographic image k, of a point in another second radiographic image i, from the information of the matrix $P_i$.

6. The process of claim 5, wherein the step for determining the projection comprises the following steps:
   determining, in a second radiographic image i, the two-dimensional coordinates of a point of interest in said radiographic image i;
   determining the beam defined by the point of interest in the image i and the optical centre of the X-ray emitter, where the beam corresponds to an epipolar line associated with the point of interest in the second radiographic image i; and
   representing, in the second radiographic image k, the epipolar line corresponding to the point of interest in the image i.

* * * * *